United States Patent [19]

Hernestam et al.

[11] 4,144,320
[45] Mar. 13, 1979

[54] AMINOALCOHOLS

[75] Inventors: Sven E. H. Hernestam; Nils A. Nilsson, both of Malmö; Lars-Olof Willard, Höllviksnäs, all of Sweden

[73] Assignee: AB Ferrosan, Malmö, Sweden

[21] Appl. No.: 786,951

[22] Filed: Apr. 12, 1977

[30] Foreign Application Priority Data

Apr. 20, 1976 [GB] United Kingdom ............... 15971/76

[51] Int. Cl.$^2$ ............................................. A61K 9/68
[52] U.S. Cl. ........................... 424/48; 260/584 R; 424/54; 424/325
[58] Field of Search ............... 424/48, 54, 325; 260/584 R

[56] References Cited

U.S. PATENT DOCUMENTS

| 1,919,298 | 7/1933 | Lehmann et al. | 424/325 |
| 2,383,564 | 8/1945 | Ralston et al. | 424/325 |
| 2,562,488 | 7/1951 | Fuchs | 424/54 |
| 2,689,170 | 9/1954 | King | 424/54 |
| 3,591,679 | 7/1971 | Voss | 424/325 |
| 3,862,308 | 1/1975 | Schmitt et al. | 424/54 |
| 3,932,605 | 1/1976 | Vit | 424/54 |
| 3,998,945 | 12/1976 | Vit | 424/54 |
| 4,006,218 | 2/1977 | Sipos | 424/54 |
| 4,059,624 | 11/1977 | Harrison | 424/54 |

Primary Examiner—Delbert R. Phillips
Attorney, Agent, or Firm—Haseltine, Lake & Waters

[57] ABSTRACT

Aminoalcohol compounds and acid addition salts thereof, useful in the prevention and treatment of dental caries and periodontitis, are disclosed. Methods of preparing said derivatives, orally acceptable compositions containing said compounds, and a method of treatment therewith are also disclosed.

7 Claims, No Drawings

AMINOALCOHOLS

The present invention relates to aminoalcohols, the process for their preparation and the use of the compounds.

The aminoalcohols provided by the invention are compounds of the general formula

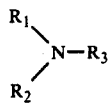    I wherein $R_1$ is H or an alkyl group, straight-chain or branched, $R_2$ is H or an alkyl group, straight-chain or branched, or a cycloalkyl group substituted by $CH_3$- to $C_5H_{11}$ groups or unsubstituted, or an alkyl group containing a cycloalkyl group substituted by $CH_3$-$C_5H_{11}$ groups or unsubstituted, and $R_1$ and $R_2$ contain 10-26 C-atoms together and $R_3$ is an alkyl group, straight-chain or branched, having 2-10 C-atoms and substituted by a hydroxy group. The sum of the C-atoms in $R_1$, $R_2$ and $R_3$ preferably between 12 and 32, inclusive.

The compounds according to the invention have valuable novel properties and can be used in the treatment of oral diseases such as periodontitis and dental caries. Said aminoalkanols are prepared as follows:

Reaction (a)

by alkylation of a secondary amine of the formula

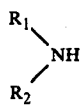    II with an alkylating agent of the formula

 $R_3X$    III (wherein $R_3$ is as hereinbefore defined and X is a reactive group, for example a halogen atom or a sulphonate ester or oxide group) or with an appropriate alkylene oxide.

Reaction (b)

from a tertiary amine of the formula

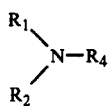    IV (wherein $R_4$ is alkyl, straight-chain or branched, and has a group convertible to or replaceable by OH or $CH_2OH$).

Reaction (b1)

$R_4$ contains halogen, $NH_2$, OAc, O—$CH_2C_6H_5$.

Reaction (b2)

$R_4$ contains COOEt, CN, CHO or is $CO(CH_2)_n$COOEt wherein n is an integer from 0 to 8.

Reaction (c)

by alkylating the secondary amine

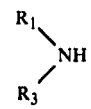    V with an alkylating agent of the formula

 $R_2X$    VI (wherein X is halogen or an organic sulphonic ester group).

Reaction (d)

from a tertiary amine of the formula

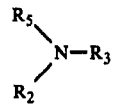    VII wherein $R_5$ contains such a group that $R_5$ is easily convertible to $R_1$.

Reaction (d1)

$R_5$ contains halogen or a double bond.

Reaction (d2)

$R_5$ contains a carbonyl group or is $CO(CH_2)_mH$ wherein m is an integer from 0 to 25.

Reaction (e)

from a tertiary amine of the formula

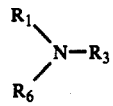    VIII wherein $R_6$ contains such a group that $R_6$ is easily convertible to $R_2$.

Reaction (e1)

$R_6$ contains halogen or a double bond.

Reaction (e2)

$R_6$ contains a carbonyl group or is

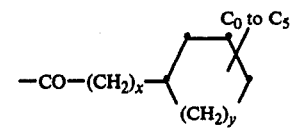

wherein the sum of x and y is from 0 to 20.

Reaction (a)

The secondary amine is reacted with a haloalkanol or an organic sulphonate ester of formula III or an alkylene oxide in an organic solvent, such as benzene or xylene. Where a haloalkanol or organic sulphonate ester of formula III is used as alkylating agent it is preferable to effect the reaction in the presence of an acid binding agent, e.g. triethylamine or potassium carbonate. Alternatively an excess of the compound of formula II may serve as acid binding agent. The reaction is preferably effected at elevated temperature, e.g., 75° to 200° C., in an autoclave.

The above described synthesis can be performed for all substituted aminoalcohols of the general formula I.

Reaction (b)

The compound

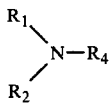

$$\begin{array}{c} R_1 \\ \diagdown \\ N-R_4 \\ \diagup \\ R_2 \end{array} \qquad IV$$

is synthesized as described in (a) (NH$_2$-groups in the side chain R$_4$ is protected by Ac). The halogen is replaced by OAc by treatment with AgOAc in HAc at 100° C. OAc may be hydrolyzed by alkali. The NHAc is hydrolyzed to NH$_2$ and the NH$_2$-group is converted to OH by treatment with NaNO$_2$ in acid solution.

CH$_2$C$_6$H$_5$ is removed by reduction in a conventional manner.

COOEt, CHO and CO(CH$_2$)$_n$ COOEt are reduced with LiAlH$_4$ in a conventional manner.

Reaction (c)

is performed under the same conditions as reaction (a).

Reaction (d)

The compound

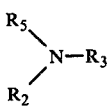

$$\begin{array}{c} R_5 \\ \diagdown \\ N-R_3 \\ \diagup \\ R_2 \end{array} \qquad VII$$

is synthesized as described in (a) (NH$_2$-groups in the R$_5$ chain are protected by Ac). The halogen is removed by treatment with LiAlH$_4$ in a conventional manner. The double bonds are removed by catalytic reduction in a conventional manner.

The carbonyl groups are removed according to Huang-Minions method and the CO-group in CO(CH$_2$)$_m$H is reduced to a CH$_2$-group with LiAlH$_4$ in a conventional manner.

Reaction (e).

The reactions are performed under the same conditions as described for reaction (d).

The compounds according to the present invention may be incorporated into preparations for dental and/or oral hygiene together with conventional carriers and excipients. Such preparations constitute a further feature of the present invention.

The oral diseases, periodontitis and dental caries, in man appear to be the result of complex biological interactions of various organisms of which the dental plaque is composed. Chronic periodontitis, perhaps the most common cause of tooth loss, is an inflammatory process of the supporting tissues of the teeth and about as prevalent as dental caries.

The development of tooth diseases has a common cause, viz, the dental plaque. The dental plaque is a deposit upon the surface of a tooth which contains for example food debris which act as a medium for a variable bacterial flora. It leads to a special structure of a harder water-insoluble plaque followed by an onset of both caries and inflammatory periodontal diseases in this region.

In the field of oral and dental hygiene there is a large variety of preparations employed as cleansing and hygienic agents for the oral activity. They may be used in tooth pastes, tablets, etc. A wide variety of chemical and biological agents have been suggested in order to retard dental plaque after it is formed or to protect the teeth against the resulting diseases. However, the mechanical removal of the dental plaque is up to now the most effective method. The chemical approach to plaque inhibition involved different groups of compounds, antibiotics, chemotherapeutics and desinfectants, fluoro compounds, organic phosphatases, chelate-forming compounds, emulsifiers, etc. Some examples are penicillin (antibiotics), chlorohexidine and 8-hydroxyquinoline (desinfectants). ethylenediamine tetraacetate (chelate-forming), NaF (strenghtening of the tooth enamel).

Some of them have too insignificant effects. Others, such as antiseptics and antibiotics, are likely to produce side effects worse than the diseases as such and still others show a certain toxicity, e.g., the fluorine compounds. (NaF may not be used as an antiplaque compound, but under strong supervision as an enamel reinforcing compound.)

It seems clear that the plaque formation is of a very complicated nature and for its chemical removal it is necessary to use compounds having a special chemical structure without pronounced antibacterial effect and having a very low toxicity.

The compounds according to the present invention have been submitted to intensive in vitro and in vivo tests and compared with reference-substances which are clinically used.

The plaque inhibiting effect has been studied in a so-called Artificial-mouth originally described by Pigman et al. (J. dent. Res. 31, 627, 1952), but later on modified (Naylor et al., "Dental Plaque," 1969); see also the Belgian patent specification No. 841,001.

Such tests with our substances have shown that they exert a clear plaque inhibiting effect, much better than chlorohexidine. Chlorohexidine has, besides its antiseptic activity, unwanted side effects, such as colouring of the teeth and development of resistance by continuous use. The test results have shown that even after 14 days no plaque has been formed.

For tests in vivo of a plaque inhibiting effect, dogs have turned out to be suitable experimental animals (Egelberg: Odont. Revy 16, 31-41, 1965).

The tests have been performed by giving the dogs hard food and several tooth-cleanings during a period of 14 days, after which the dogs have obtained a very good tooth status, i.e., clean teeth without caries; gingival pockets and other membranes of the oral cavity are clinically without objections.

After these weeks of treatment, the real test was started. The dogs were now given soft food and the tooth-cleaning was discontinued thereby creating favourable conditions for plaque forming and, later on, tooth decay.

By painting the teeth with the compounds of the invention it is possible to estimate the extent of the plaque inhibition.

Another way to register the plaque forming is to estimate, quantitatively, the increase of gingival fluid in the gingival pockets, which means that the secretion of gingival fluid increases. (Attström et al.: J. periodont. Res., Preprint 1971).

According to these criteria we have studied the effect of our compounds which have been painted on the tooth surface twice a day during a 4-week-period. As a control on the same dogs we have used physiological saline.

The visual as well as the quantitative estimations of the status of the teeth after treatment show that teeth treated with, e.g., the compound N-n-butyl-N-cetyl-6-amino-1-hexanol (Compound A) gives very low formation of plaque. It has also appeared that said compound shows very low toxicity as compared to similar compounds.

The compounds are preferably obtained and tested as hydrochlorides or hydrofluorides. They are also used in the oral preparations, although the bases or other pharmacologically acceptable salts may be used. These salts can be prepared from the bases according to conventional methods, e.g., with maleic, fumaric, succinic acids.

The preferred clinically used formulations are dentifrices, paste or powder, mouth rinses, mouthspray, chewing gum, tablets, etc. In the preparations the compounds may be used in concentrations from 0.1 to 5% and they may also be used together with other pharmacologically active substances, e.g., NaF, 6-n-amyl-m-cresol, 2,4-dichlorobenzyl alcohol.

The invention will be further clarified by the following examples.

EXAMPLE 1

N-n-butyl-hexadecanamide

An amount of 137.4 g of palmitoyl chloride in 100 ml of ethyl ether was added, under stirring at room temperature, to 80.5 g of n-butylamine in 700 ml of ethyl ether. Stirring was continued under gentle reflux for one hour. The precipitate was filtered off and thoroughly washed with water. The reaction product was recrystallized from ethanol giving 148.4 g of the title compound, melting point 74°–76° C.

EXAMPLE 2

N-n-butyl-cetylamine-hydrochloride

An amount of 101.7 g N-n-butyl-hexdecanamide was added under stirring to 25.8 g of LiAlH$_4$ suspension in 2.5 l of tetrahydrofuran. The reaction mixture was refluxed for 48 hours and then decomposed by slow addition of water and sodium hydroxide. The precipitate was filtered off. The tetrahydrofuran solution was dried and evaporated. The residue was distilled, b.p. 131°–140° C./0.06 mm Hg. Yield 86.2 g. The base was dissolved in ethyl ether and the hydrochloride precipitated with hydrochloric acid in ethyl acetate. The crude hydrochloride was recrystallized from water giving the title compound, melting point 240°–241° C.

EXAMPLE 3

N-n-butyl-N-cetyl-adipamide monomethylester

A solution of 44.5 g of adipoyl chloride monomethylester in 120 ml of toluene was added dropwise, at 20°–25° C., to a mixture of 80 g of N-n-butyl-cetylamine and 27.7 g of triethylamine in 500 ml of toluene. The reaction mixture was stirred at room temperature for 18 hours. The toluene solution was washed with water, dried over Na$_2$SO$_4$ was evaporated. Removal of the toluene gave the crude titel compound. Yield 109.8 g.

EXAMPLE 4

N-n-butyl-N-cetyl-6-amino-1-hexanol (Compound A)

An amount of 88.2 g of crude N-n-butyl-N-cetyl-adipamide monomethylester in 600 ml of ethyl ether was added under stirring to 53.9 g of LiAlH$_4$ suspension in 2 l of ethyl ether. The reaction mixture was refluxed for 65 hours and then decomposed by slow addition of water and sodium hydroxide. The precipitate was filtered off. The ether solution was dried and evaporated. The residual oil was distilled giving 62.6 g of the title compound, boiling point 155°–157° C./0.03 mm Hg. The base was dissolved in ether and the hydrochloride precipitated with hydrochloric acid in ethyl acetate. After recrystallization from ethyl acetate the melting point is 58°–59° C.

EXAMPLE 5

N-Ethyl-N-n-octyl-ethanolamine

A mixture of 15.7 g of ethyl-n-octylamine, 5 g of ethyleneoxide and 100 ml of 96% ethanol was held at 100° C. for one hour in a steel autoclave. The reaction mixture was distilled and gave 16.2 g of N-ethyl-N-n-octyl-ethanolamine, b.p. 85°–87° C./0.2 mm Hg, n$_D^{22}$ = 1.4490.

The hydrochloride is not crystalline.

EXAMPLE 6

N,N-Di-n-octyl-3-amino-1-propanol

A mixture of 24 g of di-n-octylamine, 10 g of 3-chloro-1-propanol and 11 g of triethylamine in 200 ml of toluene was refluxed for 24 hours. The toluene solution was washed twice with water to remove the triethylamine hydrochloride formed and then evaporated. The residue was distilled and gave 19.9 g of N,N-di-n-octyl-3-amino-1-propanol, b.p. 125°–130° C./0.01 mm Hg, n$_D^{22}$ = 1.4613.

The hydrochloride is not crystalline.

EXAMPLE 7

| Tooth paste Ingredients | Amounts |
| --- | --- |
| Compound A | 2% by weight |
| Dicalcium phosphate | 50% |
| Sorbitol | 6% |
| Glycerol | 18% |
| Na-carboxymethylcellulose | 2% |
| Na-lauryl sulphate | 1% |
| Na-saccharin | 0.1% |
| Peppermint oil | 0.9% |
| Water up to | 100% |

EXAMPLE 8

| Chewing gum | Amounts |
| --- | --- |
| Core | |
| Compound A | 2% by weight |
| Fructose | 50% |
| Glycerol | 5% |
| Mannitol | 30% |
| Gum base | 2% |
| Carboxymethylcellulose | 10% |
| Sodium cyclamate | 1% |
| Coating | |
| Carnauba wax containing: | |
| Fructose | 9% by weight |
| Gum arabic | 5% |
| Dextrin | 2% |
| Flavour | 2% |
| (The core materials are mixtured at 50° C.) | |

EXAMPLE 9

| A chewable tablet | Amounts |
| --- | --- |
| Compound A | 20 grams |
| Sorbitol | 800 |
| Potato starch | 150 |
| 5% aq. sol. of gelatin | 30 |
| Peppermint oil | — |
| Na-cyclamate | 2 |

| A chewable tablet | Amounts |
|---|---|
| Na-saccharin | 1 |
| are tabletted to | |
| 1000 tablets with 2% of compound A. | |

EXAMPLE 10

| Mouth rinse liquid | Amounts |
|---|---|
| Compound A | 1% by weight |
| Glycerol | 10% |
| Ethanol | 15% |
| Na-cyclamate | 1.0% |
| Na-saccharin | 0.1% |
| Menthol-flavour | 0.1% |
| Water | ad 100 |

Table 1

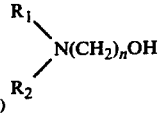

$$\begin{array}{c} R_1 \\ \diagdown \\ N(CH_2)_n OH \\ \diagup \\ R_2 \end{array}$$

| $R_1$ | $R_2$ | n | Mp[a]/bp, °C | $n_D^{22\ b)}$ | PIE[e] |
|---|---|---|---|---|---|
| n-$C_8$ | $C_2$ | 2 | 85/0.2 mm Hg | 1.4490 | (+) |
| n-$C_8$ | $C_2$ | 6 | 78–81 | | + |
| n-$C_8$ | n-$C_4$ | 3 | 115–118/0.6 mm Hg | 1.4510 | ++ |
| n-$C_8$ | n-$C_4$ | 4 | 126–128/0.6 mm Hg | 1.4545 | (+) |
| n-$C_8$ | n-$C_5$ | 2 | 100–105/0.05 mm Hg | 1.4502 | +++ |
| n-$C_8$ | n-$C_5$ | 5 | 90–100/0.05 mm Hg | 1.4570 | +++ |
| n-$C_8$ | n-$C_8$ | 2 | 98/0.1 mm Hg | 1.4543 | +++ |
| n-$C_8$ | n-$C_8$ | 3 | 125–130/0.1 mm Hg | 1.4613 | +++ |
| n-$C_8$ | $C_6$ [c] | 4 | 148–150/0.4 mm Hg | 1.4746 | (+) |
| n-$C_{10}$ | n-$C_4$ | 3 | 114–117/0.2 mm Hg | 1.4542 | +++ |
| n-$C_{10}$ | n-$C_4$ | 4 | 121–124/0.2 mm Hg | 1.4572 | +++ |
| n-$C_{10}$ | $C_4$ [d] | 3 | 93–95/0.01 mm Hg | 1.452 | +++ |
| n-$C_{10}$ | $C_4$ [d] | 4 | 110–112/0.01 mm Hg | 1.454 | +++ |
| n-$C_{11}$ | $C_2$ | 4 | 90–92 | | +++ |
| n-$C_{11}$ | $C_2$ | 5 | 71–73 | | ++ |
| n-$C_{11}$ | $C_2$ | 6 | 98–100 | | ++ |
| n-$C_{14}$ | $C_4$ [d] | 3 | 53–54 | | +++ |
| n-$C_{14}$ | $C_4$ [d] | 4 | 57–58 | | +++ |
| n-$C_{16}$ | $C_2$ | 2 | 76–78 | | +++ |
| n-$C_{16}$ | $C_2$ | 4 | 92–94 | | +++ |
| n-$C_{16}$ | n-$C_4$ | 4 | 59–60 | | + |
| n-$C_{16}$ | n-$C_4$ | 6 | 58–59 | | +++ |
| | | | 155–157/0.03 mm Hg | 1.4620 | +++ |
| n-$C_{18}$ | n-$C_8$ | 2 | 80–82 | | + |
| n-$C_{18}$ | n-$C_8$ | 4 | 60–62 | | + |

Table 1-continued $$\begin{array}{c} R_1 \\ \diagdown \\ N(CH_2)_n OH \\ \diagup \\ R_2 \end{array}$$

| $R_1$ | $R_2$ | n | Mp[a]/bp, °C | $n_D^{22\ b)}$ | PIE[e] |
|---|---|---|---|---|---|
| n-$C_{18}$ | n-$C_8$ | 6 | 54–56 | | (+) |

[a] Hydrochloride salt (melting points are uncorrected)
[b] Base
[c] Cyclohexyl
[d] Isobutyl
[e] +++ = very good activity
++ = good activity
+ = fair activity
(+) = weak activity
PIE = plaque inhibiting effect
Compound A = N-n-butyl-N-cetyl-6-amino-1-hexanol

We claim:

1. A compound consisting of N-n-butyl-N-cetyl-6-amino-1-hexanol.

2. An agent for use in the treatment of the oral cavity and on tooth surfaces to inhibit plaque formation consisting essentially from 0.1 to 5% of a substance active for plaque inhibition selected from the group consisting of N-n-butyl-N-cetyl-6-amino-1-hexanol and pharmaceutically acceptable acid addition salts thereof in a pharmaceutically acceptable carrier conventionally used for cleansing and hygienic purposes in the oral cavity.

3. An agent according to claim 2, wherein said active substance is in the form of a solution in a carrier conventionally used for cleansing and hygienic purposes in the oral cavity.

4. An agent according to claim 2, wherein said active substance is in the form of a suspension in a carrier conventionally used for cleansing and hygienic purposes in the oral cavity.

5. An agent according to claim 2, wherein said active substance is in the solid form admixed with a carrier conventionally used for cleansing and hygienic purposes in the oral cavity.

6. An agent according to claim 2, wherein said carrier for cleansing and hygienic purposes in the oral cavity is selected from the group consisting of tooth paste, mouth rinse liquid, chewing gum and chewable tablets.

7. A method of treatment for inhibiting plaque of the oral cavity and on tooth surfaces which comprises using an effective amount of a substance active in plaque inhibition selected from the group consisting of N-n-butyl-N-cetyl-6-amino-1-hexanol and pharmaceutically acceptable acid addition salts thereof.

* * * * *